United States Patent [19]
Edwards

[11] Patent Number: 6,002,968
[45] Date of Patent: Dec. 14, 1999

[54] UTERINE TREATMENT APPARATUS

[75] Inventor: Stuart D. Edwards, Portola Valley, Calif.

[73] Assignee: Vidacare, Inc., Sunnyvale, Calif.

[21] Appl. No.: 09/064,690

[22] Filed: Apr. 22, 1998

Related U.S. Application Data

[63] Continuation-in-part of application No. 08/731,372, Oct. 11, 1996, which is a continuation-in-part of application No. 08/319,373, Oct. 6, 1994, Pat. No. 5,575,788, which is a continuation-in-part of application No. 08/286,862, Aug. 4, 1994, Pat. No. 5,558,672, which is a continuation-in-part of application No. 08/272,162, Jul. 7, 1994, Pat. No. 5,569,241, which is a continuation-in-part of application No. 08/265,459, Jun. 24, 1994, Pat. No. 5,505,730.

[51] Int. Cl.$^6$ .................................................. A61B 17/36
[52] U.S. Cl. .................... 607/101; 607/105; 607/156; 606/41
[58] Field of Search ..................... 606/41, 42, 48–50; 607/100–102, 104, 105, 156

[56] References Cited

U.S. PATENT DOCUMENTS

| | | | |
|---|---|---|---|
| 5,505,730 | 4/1996 | Edwards | 606/41 |
| 5,531,662 | 7/1996 | Carr | 600/2 |
| 5,776,176 | 7/1998 | Rudie | 607/101 |
| 5,800,486 | 9/1998 | Thome et al. | 607/105 |
| 5,830,213 | 11/1998 | Panescu et al. | 606/41 |

*Primary Examiner*—Michael Peffley
*Attorney, Agent, or Firm*—Wilson Sonsini Goodrich & Rosati

[57] ABSTRACT

An apparatus to treat a uterus includes a deployable member configured to be positioned in a uterine cavity in at least a partially deployed state to define a microwave chamber in an interior of the deployable member, and removed from the uterine cavity in a non-deployed state. The deployable member is at least partially microwave energy absorbable and formed of a fluid permeable material to house and controllably release a fluidic medium from the microwave chamber when the deployable member is positioned in the uterine cavity in the at least partially deployed state. A microwave emitter is positioned in the microwave chamber, the microwave emitter is configured to be coupled to a microwave energy source and deliver microwave energy to the fluidic medium, wherein the fluidic medium transfers thermal energy from the microwave emitter to a uterine structure.

66 Claims, 16 Drawing Sheets

UTERINE TREATMENT APPARATUS

CROSS-REFERENCE TO RELATED APPLICATIONS

This application is a continuation-in-part of U.S. patent application Ser. No. 08/731,372, filed Oct. 11, 1996, which is a continuation-in-part of U.S. patent application Ser. No. 08/319,373, filed Oct. 6, 1994, now U.S. Pat. No. 5,575,788, which is a continuation-in-part of U.S. application Ser. No. 08/286,862, filed Aug. 4, 1994, now U.S. Pat. No. 5,558,672 which is a continuation-in-part of U.S. patent application Ser. No. 08/272,162, filed Jul. 7, 1994, now U.S. Pat. No. 5,569,241, which is a continuation-in-part of U.S. patent application Ser. No. 08/265,459, filed Jun. 24, 1994, now U.S. Pat. No. 5,505,780, all of which are incorporated by reference.

BACKGROUND OF THE INVENTION

1. Field of the Invention

This invention relates generally to a method and apparatus to controllably create controlled necrosis of at least a portion of the uterus, and more particularly to a method and apparatus to create selective cell necrosis of target sites of the uterus.

2. Description of Related Art

There are a number of body organs and lumens, including but not limited to the uterus, gall bladder, large intestine and the like, that have inner layers that develop disease states or otherwise abnormal conditions which can cause discomfort to the patient and are precursors to disease states. Traditional methods of treatment for these conditions have included removal all or a major portion of the body organ (e.g. hysterectomy).

Menorrhagia an abnormality of the uterus, is an example of such a disease state. It is characterized by excessive menstrual bleeding of the endometrium in the absence of organic pathology. While the disease has no known aetiology, it has been postulated that it is due to an inappropriate exposure of the endometrium to hormones. Approximately 10% of all women in the US experience menorrhagia and it is responsible for approximately one in five outpatient referrals to gynecological departments. At a minimum, the disease can cause considerable discomfort, distress and curtailment of lifestyle. Women suffering severe menorrhagia are at risk from chronic anemia and other complications. Moreover, it is the most frequent clinical indication for hysterectomy.

While there are a number of available treatments for the disease, many have limitations and/or potentially adverse complications. For example, currently available pharmacological therapy requires the long term administration of medication, which in some case provides only temporary beneficial effects while presenting potentially long term adverse side effects. Hysterectomy is another common treatment, but the associated morbidity and convalescence period can be prolonged, making this treatment an undesirable choice for some patients.

A number of physical and chemical methods have been tried as alternatives to hysterectomy, including the use of superheated steam, cryotherapy, urea injection and radium packing. The most commonly used methods as an alternative to hysterectomy are, ablation of the endometrium either by using a laser, such as a Nd:YAG laser, or the use of RF energy applied with an electrode.

Laser treatments have provided only limited success. RF is an attractive alternative. In RF heating, a conductive probe is placed within the uterine cavity and an insulated ground-plane electrode or belt is placed around the patient's midriff. RF energy is applied to the thermal probe with the external belt electrode acting as the return arm of the circuit. The electrical load presented by the RF thermal probe, patient, and external belt is matched to the output of the RF generator via a tuning unit, to form a series resonant circuit. Once tuned, the majority of the power applied to the probe is deposited into the endometrium as heat.

Current flows primarily capacitively, and an electric field is set up around the active tip of the probe. Tissue lying within the field becomes heated because of rapid oscillation of charged particles and locally induced currents.

Prior et al. have reported on the use of RF to treat menorrhagia. Power at 27·12 MHz was delivered to a probe that was placed into the uterine cavity and capacitively coupled to a second electrode consisting of a belt placed around the patient (Prior et al., Int. J. Hyperthermia, 1991, Vol. 7, No. 2, pgs. 213 to 220). The active electrode was a 10 mm diameter stainless-steel cylinder with a length of 70 mm. This method, however, did not adequately deliver RF energy to the entire endometrium. Because the endometrium has an irregular surface, it is difficult to deliver sufficient RF energy to the entire structure and effectively treat menorrhagia.

However, it is desirable to have close contact between the RF conductive face and the endometrium. In U.S. Pat. No. 5,277,201 (the "'201 patent") an electroconductive, expandable balloon expands the interior of the uterus and effects electrical contact with the endometrial lining to be destroyed. The device of the '201 patent fails, however, to provide sufficient physical contact with the entire endometrium, and thus the treatment is not complete. Not only is the physical contact with the endometrium unsatisfactory, but the effective delivery of RF energy to the endometrium could be improved as well.

There is a need to provide a method and apparatus to minimally invasively treat the uterus. There is a another need for a method and apparatus to minimally invasively treat selected sites of the uterus. There is a further need for a method and apparatus to selectively treat endometriosis and/or fibroids. There is yet another need for a method and apparatus to deliver sufficient energy to treat a substantial portion of the uterus.

SUMMARY OF THE INVENTION

Accordingly, an object of the invention is to provide a method and apparatus to minimally invasively treat the uterus.

Another object of the invention is to provide a method and apparatus to minimally invasively treated selected sites of the uterus.

A further object of the invention is to provide a method and apparatus to selectively treat endometriosis.

Another object of the invention is to provide a method and apparatus to selectively treat fibroids.

Still another object of the invention is to provide a method and apparatus to deliver sufficient energy to treat a substantial portion of the uterus.

Another object of the invention is to provide an easy to use method and apparatus to selectively create cell necrosis in the uterus.

These and other objects of the invention are achieved in an apparatus to treat a uterus comprising a deployable member configured to be positioned in a uterine cavity in at least a partially deployed state to define a microwave chamber in an interior of the deployable member, and removed from the uterine cavity in a non-deployed state. The deployable member is at least partially microwave energy absorbable and formed of a fluid permeable material to house and controllably release a fluidic medium from the microwave chamber when the deployable member is positioned in the uterine cavity in the at least partially deployed state. A microwave emitter is positioned in the microwave chamber, the microwave emitter being configured to be coupled to a microwave energy source and deliver microwave energy to the fluidic medium, wherein the fluidic medium transfers thermal energy from the microwave emitter to a uterine structure.

DETAILED DESCRIPTION

Figure 1:
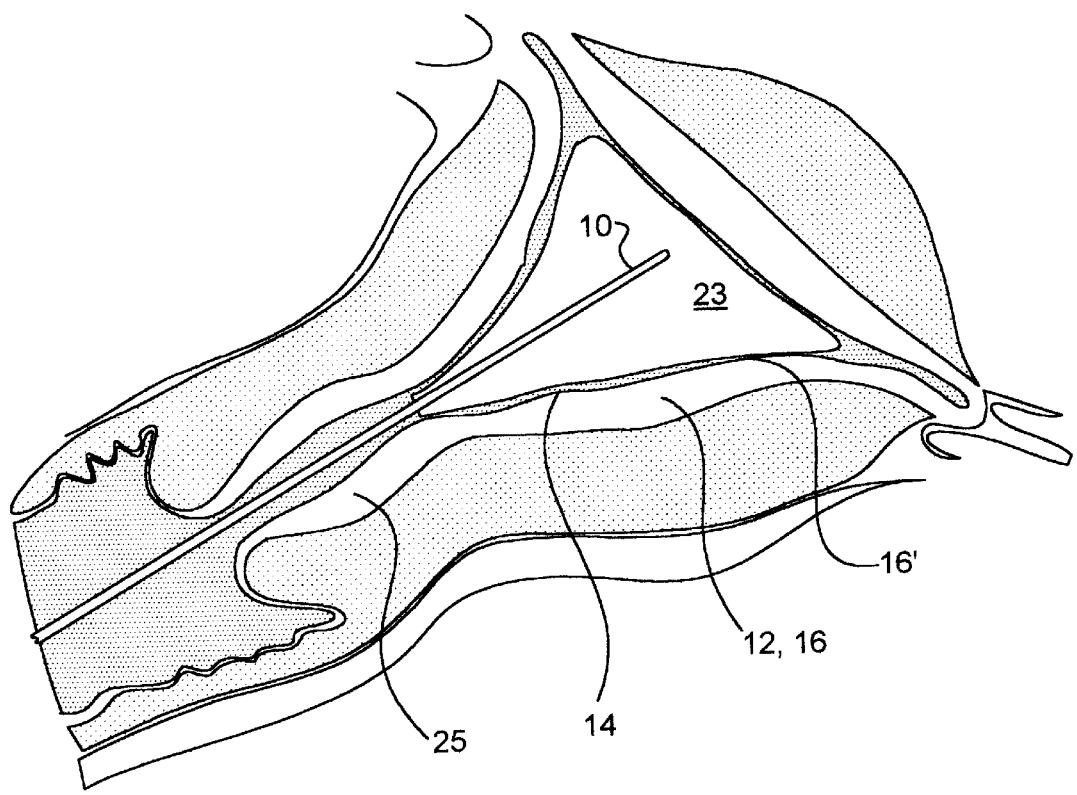
FIG. 1 is a lateral view of the uterine cavity illustrating positioning of the uterine treatment apparatus of the present invention in the uterus.
Figure 2A:
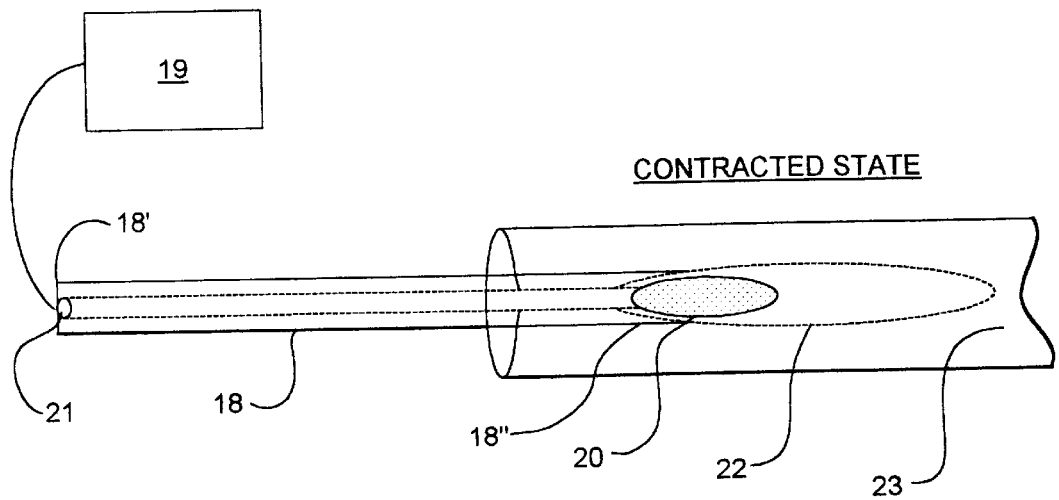
FIGS. 2B and 2A are lateral view of the present invention illustrating the introducer, introducer lumens, microwave chamber, fluid circuit and expansion device in an expanded and contracted state, respectively.
Figure 2B:
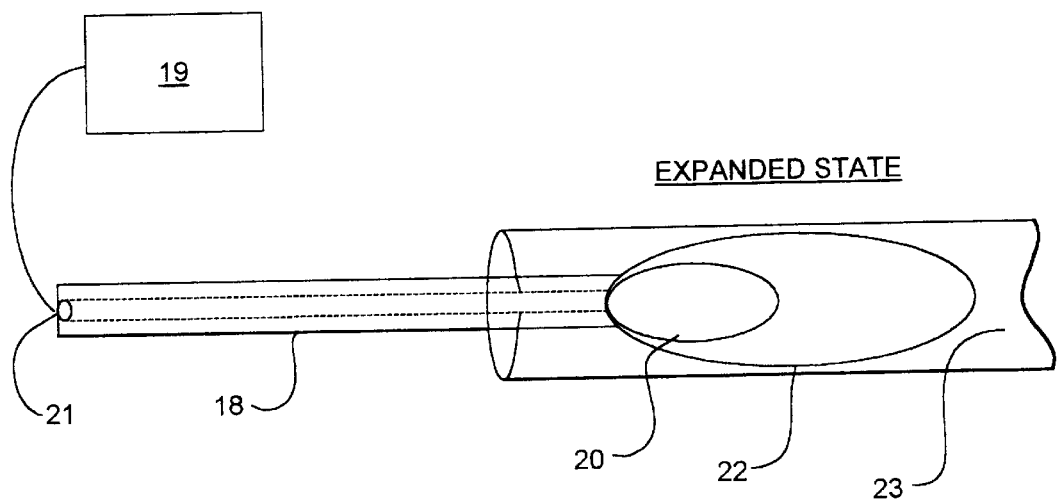

Referring now to FIGS. 1 and 2, one embodiment of uterine treatment apparatus 10 that is used to deliver thermal energy to a treatment site 12 and produce thermal injury zones 14 in endometrium 16, includes a flexible introducer 18, coupled to a microwave chamber 20 and a conforming member 22, also called expandable member 22. Endometrium 16 comprises a surface layer of cells 16' (also called endometrial surface 16') that line the interior of the uterus 23. The apparatus of the present invention provides an improved means for the selected necrosis of these cells and other areas within uterus 23.

As shown in FIG. 2, introducer 18 has proximal and distal ends 18' and 18". In one embodiment of the present invention, a fluid source 19 is fluidicaly coupled to introducer 18 at or near its proximal end 18' while expandable member 22 is coupled at or near introducer distal end 18'. Fluid source 19 may be any one of a number controllable fluid pumps well known to those skilled in the art such as a peristaltic or positive displacement pump, versions of which are manufactured by the Cole Palmer Company. Introducer 18 has sufficient length to position microwave chamber 20 and expandable member 22 in the uterus 23 using a vaginal approach. Typical lengths for introducer 18 include, but are not limited to, a range between 2 to 20 cm. Introducer 18 is also sized to be able to enter the cervix 25 without significant resistance and/or the need to heavily anesthetize the patient. In various embodiments, introducer 18 is flexible, articulated and steerable. Introducer 18 may have one or more lumens 21, that extend the full length of introducer 18, or only a portion thereof. Lumens 21 may be used as paths for the delivery of fluids and gases, as well as providing channels for cables, catheters, guide wires, pull wires, insulated wires, and optical fibers. In one embodiment, introducer 18 can be a multi-lumen catheter, as is well known to those skilled in the art.

Figure 3:
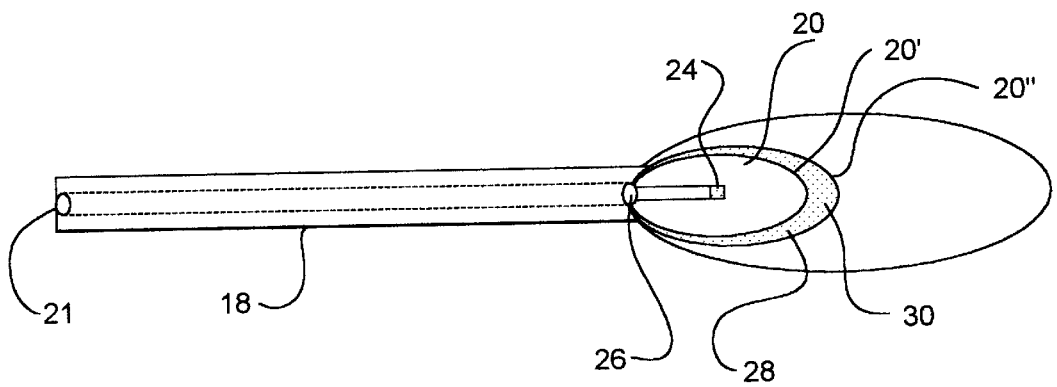
FIG. 3 is an enlarged lateral view illustrating the composition of the microwave chamber.

Referring now to FIG. 3, microwave chamber 20 includes an interior surface 20' an exterior surface 20", a microwave antenna 24, a proximal aperture 26, a microwave reflector 28 and microwave shielding 30. Microwave reflector 28 serves to focus microwaves within microwave chamber 20 and to reduce microwave energy losses from microwave chamber 20. This results in a more efficient conversion of microwave energy to thermal energy, which is used to heat a heat transfer fluid that will be discussed herein. Microwave reflectors 28 can include aluminum and other dichroic materials known to those skilled in the art. Microwave shielding 30 serves to minimize and/or prevent microwave energy from radiating out of microwave chamber 20 and includes materials such as polyiron, teflon®, polyvinyl chloride, silicon carbide fibers and other microwave energy absorbing materials known to those skilled in art. Microwave shielding can also be applied to all or a portion of introducer 18.

Figure 4:
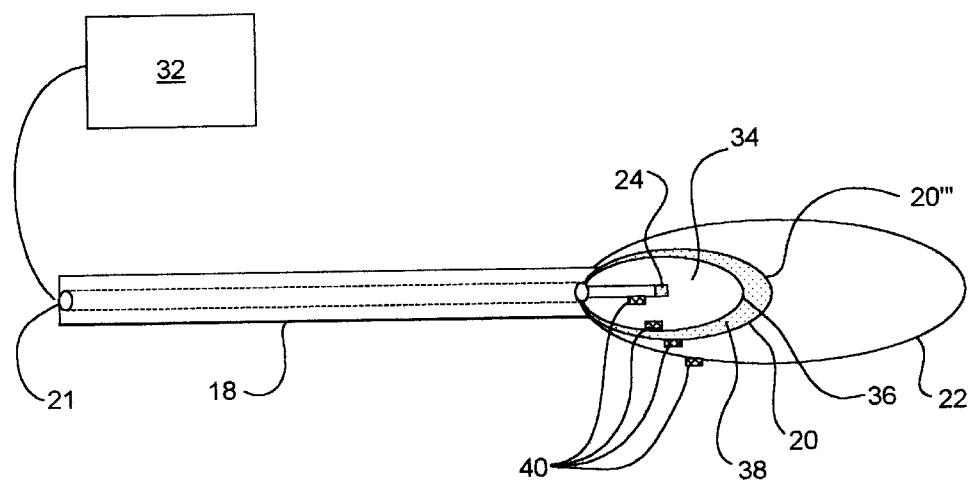
FIG. 4 is an enlarged lateral view of the microwave chamber illustrating the use of the microwave chamber to heat a heat transfer medium.

Referring now to FIG. 4, microwave chamber 20 is configured to be coupled to a microwave power source 32. Microwave chamber 20 is further configured to receive a fluidic medium, also called a heat transfer medium 34, from introducer 18, heat said fluid via microwave heating from microwave antenna 24 and subsequently delivery heat transfer fluid to exterior surface 20" of chamber 20 via pores, or channels 36 in microwave chamber wall 20'". In one embodiment of the invention, microwave chamber wall 20'", (including shielding and reflective layers 28 and 30) can be constructed of porous materials 38. Typical materials for porous materials 38 include, but are not limited to, expanded PTFE (teflon); and silicon carbide woven fibers such as Nicalon® and Nextel®. Use of porous materials 38 allows heat transfer fluid 34 to permeate through microwave chamber wall 20' under the influence of capillary action and/or a pressure head provided by fluid source 19.

Microwave energy emitted by antenna 24 causes oscillation and friction of the molecules of heat transfer medium 34. As a result of this intermolecular friction, high-frequency energy absorbed by heat transfer medium 34 is transformed into thermal energy, resulting in a temperature rise of heat transfer medium 34. The heating effect is enhanced in electrolyte and salt solutions. Accordingly, solutions for heat transfer medium 34 include, but are not limited to, water, electrolyte and salt solutions.

Microwave chamber 20 may contain one or more sensors 40 for sensing physical properties of heat transfer medium 34 within, on, or adjacent to microwave chamber 20. Such physical properties include temperature, electrical conductivity, electrical capacitance, thermal conductivity, density, flow rate, strength, elasticity, moisture content, optical reflectance, optical transmittance, optical absorption, acoustical impedance and acoustical absorption. Sensors 40 can be located in one or more of the following locations: i) on antenna 24, ii) on the exterior or interior surfaces 20" and 20' of microwave chamber 20 iii) within microwave chamber wall 20''', or iv) on expandable member 22. Suitable sensors that may be used for sensors 40 include: i) thermocouples, ii) fiber optics, iii) photomultipliers, iv) resistive wires, v) thermocouple IR detectors, vi) thin film sensors, vii) anemometric sensors, and viii) ultrasound sensors; all known to those skilled in the art. Sensors 40 may also be electronically coupled to fluid source 19 and a control system 44 discussed herein order to control the flow rate and/or fluidic pressure of heat transfer medium in microwave chamber 20.

Figure 5:
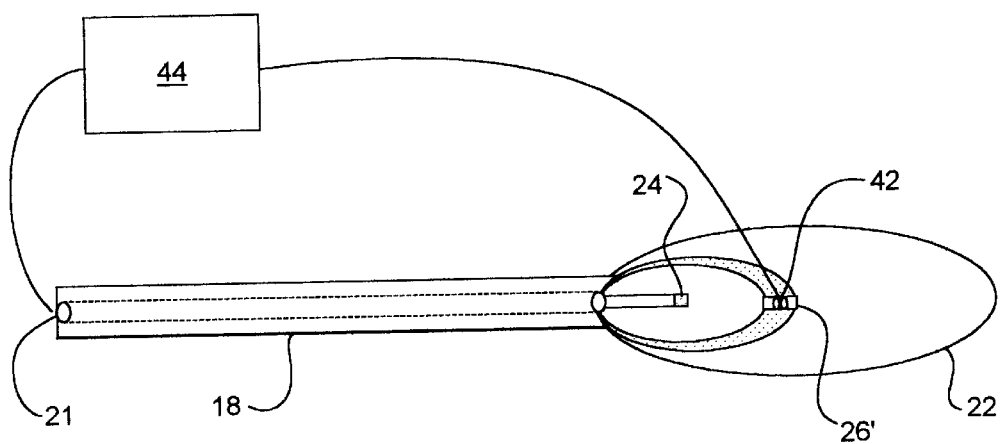
FIG. 5 is an enlarged lateral view illustrating the use of valves in the microwave chamber to control the flow of heat transfer medium.

In another embodiment of the invention depicted in FIG. 5, microwave chamber 20 includes a distal aperture 26' and a valve 42. Valve 42 may be electronically coupled to control system 44 and may also be controllable by the physician. Valve 42 may be a self actuating pressure-controlled one-way valve, such as a Bunsen valve, designed to open at a set pressure, or a self actuating thermostatically-controlled valve designed to open at a set temperature, or an electronically-controlled valve coupled to control system 44 discussed herein all of which are well known to those skilled in the art. In one embodiment, valve 42 opens when a given temperature or pressure is reached inside microwave chamber allowing heat transfer medium 34 to flow out of microwave chamber 20 into expandable member 22 or uterus 23. Valve 42 may also be opened under control of the physician. In alternative embodiments, valve 42 is opened by control system 44 using another set of control criteria programmable into control system 44 including, but not limited to, a rate of temperature increase, a rate of pressure increase, residence time in microwave chamber 20, or a combination of one or more of the preceding criteria.

Expandable member 22 is sized to be able to fit through cervix 25 in a non-deployed state without significant resistance. To facilitate passage of expandable member 22 through the cervix in its non-deployed state, expandable member 22 can be wrapped or folded around introducer 18 or another supporting member. Typical external diameters for expandable member 22 in a non deployed state include, but are not limited to, a range from 1 to 4 mms. When in the deployed state, expandable member 22 expands sufficiently such that the external surface 22' of conforming member 22 is engaged with all or a portion of endometrial surface 16'. The typical volume for expanded expandable member 22 is in a range that includes but is not limited to, values between 2 and 8 cubic centimeters.

Figure 6:
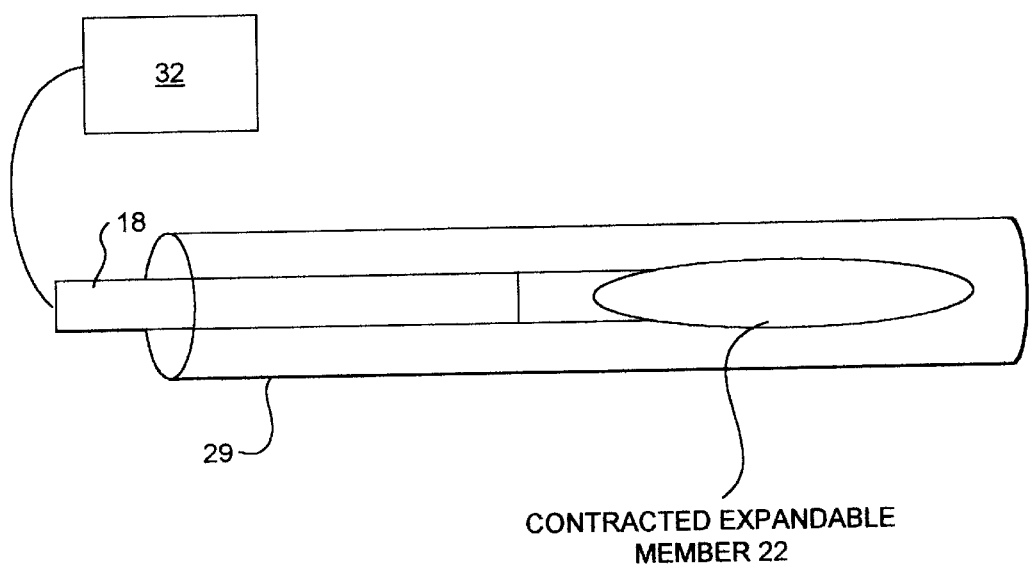
FIG. 6 is an lateral view illustrating the use of a sheath to house the expandable member.

Referring now to FIG. 6, in one embodiment of the invention, expandable member 22 can be disposed in its non-deployed state in a sheathing member 29, also called sheath 29, that extends over all or part of introducer 18. Once expandable member 22 has been properly positioned in uterus 23, sheath 29 is pulled back proximally, allowing expandable member 22 to be deployed in uterus 23. In various embodiments, sheath 29 is flexible, articulated and steerable and contains a continuous lumen of sufficient diameter to allow the advancement of introducer 18. Typical diameters for sheath 29 include 0.05 to 0.5 inches. Suitable materials for sheath 29 include coil-reinforced plastic tubing as is well known to those skilled in the art.

Figure 7:
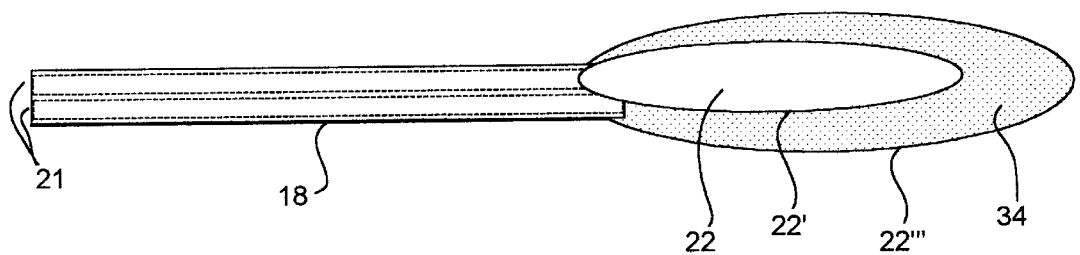
FIG. 7 is an lateral view illustrating the use of a second expandable member.

Expandable member 22 is made of a material that suitably conforms to the organ or tissue surface to be treated. This improves the engagement of expandable member 22 with endometrial surface 16' and in so doing, enhances the delivery of energy to treatment site 12. Typical thicknesses for the material used in expandable member 22 include, but are not limited to, a range from 0.0005 to 0.050". Also, expandable member 22 can have apertures 36 for the flow of heat transfer medium 34 to uterine wall 23'. Alternatively, expandable member 22 can be made of a microporous material that does not include distinct apertures. General material types for expandable member 22 include elastomeric polymers, porous polymers, foam materials or a combination thereof. Specific materials include but are not limited to, knitted polyester, continuous filament polyester, polyester-cellulose, rayon, polyimide, polyurethane, polyethylene, silicone, expanded teflon, and the like. Suitable commercial foams include: (i) Opcell, available from Sentinel Products Corp., Hyannis, Mass. and (ii) UltraSorb, HT 4201 or HT 4644MD from Wilshire Contamination Control, Carlsbad, Calif. Expandable member 22 has characteristics that make it particularly moldable and formable to irregular surfaces. In one embodiment, expandable member 22 is made of an open cell foam, or alternatively it can be a thermoplastic film such as polyurethane, low density polyethylene, or it may be a silicone. Referring now to FIG. 7, a second expandable member 22" can be coupled to first expandable member 22 such that first expandable member 22 is disposed inside of second expandable member 22". In various other embodiments, second expandable member 22" can be positioned proximal or to distal to first expandable member 22 and in fluid communication with first expandable member 22 via lumens 21. Second expandable member 22" receives at least a portion of heat transfer medium 34 from exterior surface 22' of first expandable member 22.

Figure 8A:
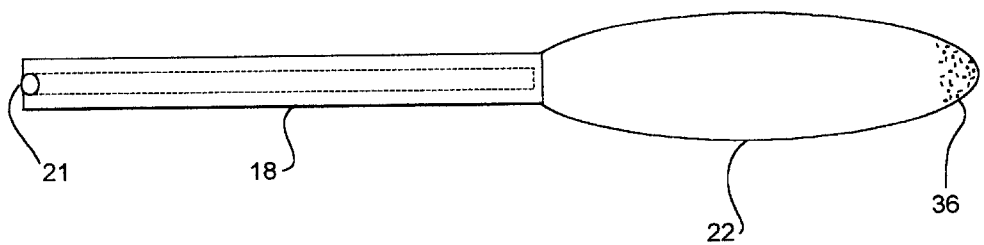
FIGS. 8A, 8B and 8C are lateral views illustrating the placement of pores on the expandable member.
Figure 8B:
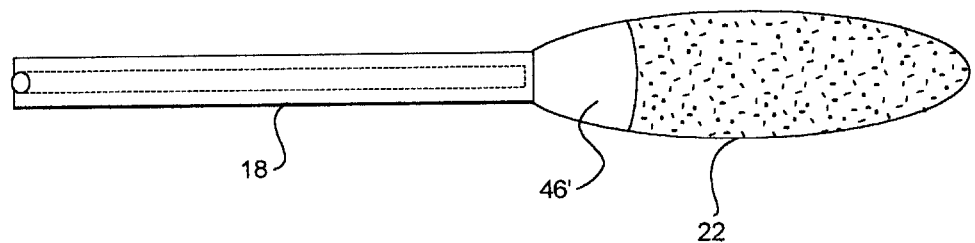
Figure 8C:
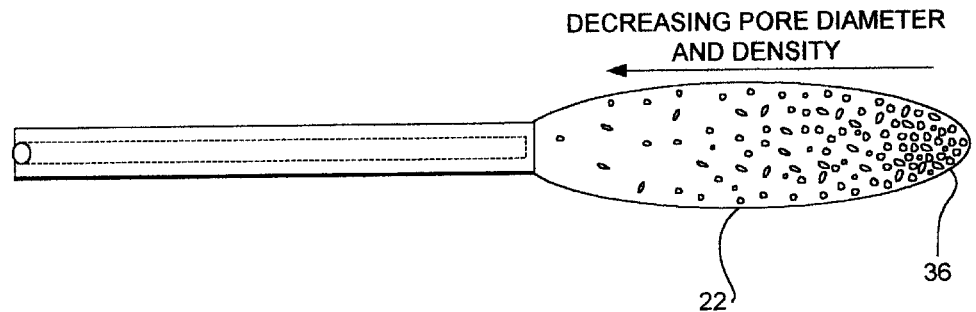

Turning now to a discussion of the placement of pores 36 in expandable member 22, pores 36 may be located on all, or only a portion, of expandable member 22 in areas called porous zones 46'. Upon application of sufficient pressure (supplied by fluid source 19), heat transfer medium permeates 34 out of pores 36 in first and/or second expandable member 22 and 22" and makes contact with uterine wall 23'. Referring now to FIGS. 8A, 8B and 8C, in various embodiments of the invention, pores 36 may be located over discrete areas of expandable member 22 in order to control the immediate area of uterine wall 23' contacted by heat transfer medium 34 and hence the area of thermal injury zone 14. As shown in FIG. 8A, pores 36 are positioned only on the distal half of expandable member 22, so as to minimize the heating of the lower half of uterine wall 23'. In another embodiment shown in FIG. 8B, pores 36 are located over most of the surface of expandable member 22, except for a non-porous zone 46' of sufficient area to prevent heating tissue in uterine wall within several centimeters of the cervix 25. In this case, non-porous zone 46' extends 0.5 to 3 cm past the distal end 18" of introducer 18. In another embodiment shown in 8C, pores 36 may be distributed across the surface of expandable member 22 in a pattern of varying pore diameter and pore density, such that pore density and diameter are greatest at the distal end of expandable member 22 with both decreasing in the proximal direction. The directional gradients of pore density and diameter on expandable member 22 are configured to allow the physician to be able to select the area of expandable member 22 that weeps heat transfer medium 34 by raising or lowering the pressure that is applied to expandable member 22 by fluid source 19. Specifically, lower pressures cause only the distal area of expandable member 22 to weep heat transfer medium 34 with increasing fluid pressure increasing this area in a proximal direction.

Figure 9:
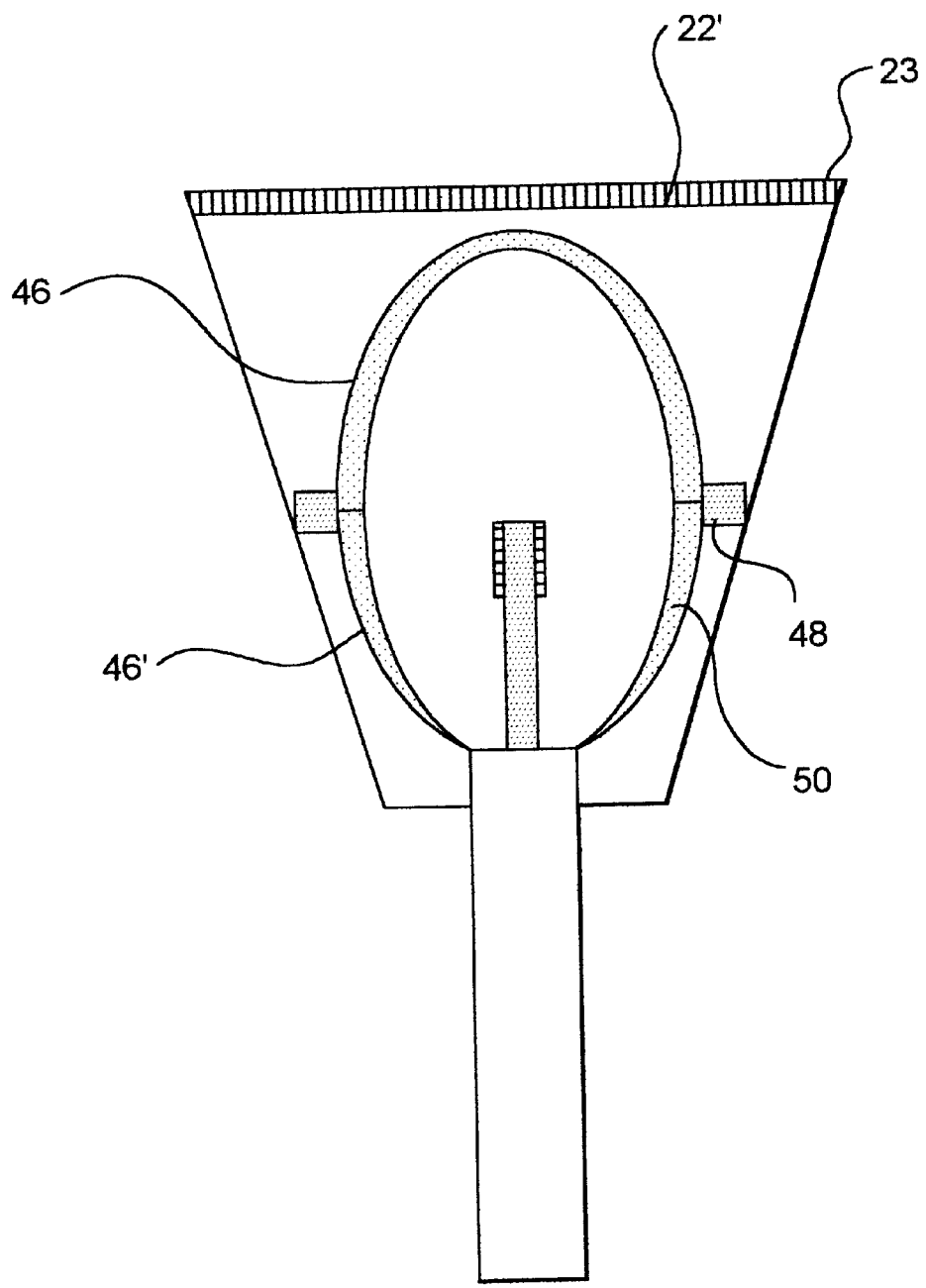
FIG. 9 is a lateral view illustrating the expandable member in a fully deployed state inside the uterus and the use of a raised lip and insulating sections to contain endometrial heating to discrete areas of the uterus.

Referring now to FIG. 9, in order to facilitate the creation of discrete thermal injury zones 14 in uterine wall 23', expandable member 22 is fully inflated inside the uterus to engage the uterine wall and prevent the flow of heat transfer medium to areas of the uterus not contacted by porous sections of expandable member 22. For the same purpose, expandable member 22 may contain a raised lip 48 that impedes/prevents the flow of heat transfer medium to sections of the uterine wall not contacted by porous sections of expandable member 22. Lip 48 is located adjacent to the boundary between porous zone 46 and nonporous zone 46'. Continuing in this regard, to minimize the conduction of unwanted heat through expandable member 22, expandable member may contain a thermally insulating layer 50 over all, or part, of its surface area. Suitable materials for thermally insulating layer 50 include teflon, Thinsulate® and other thermal insulators known to those skilled in the art.

Figure 10:
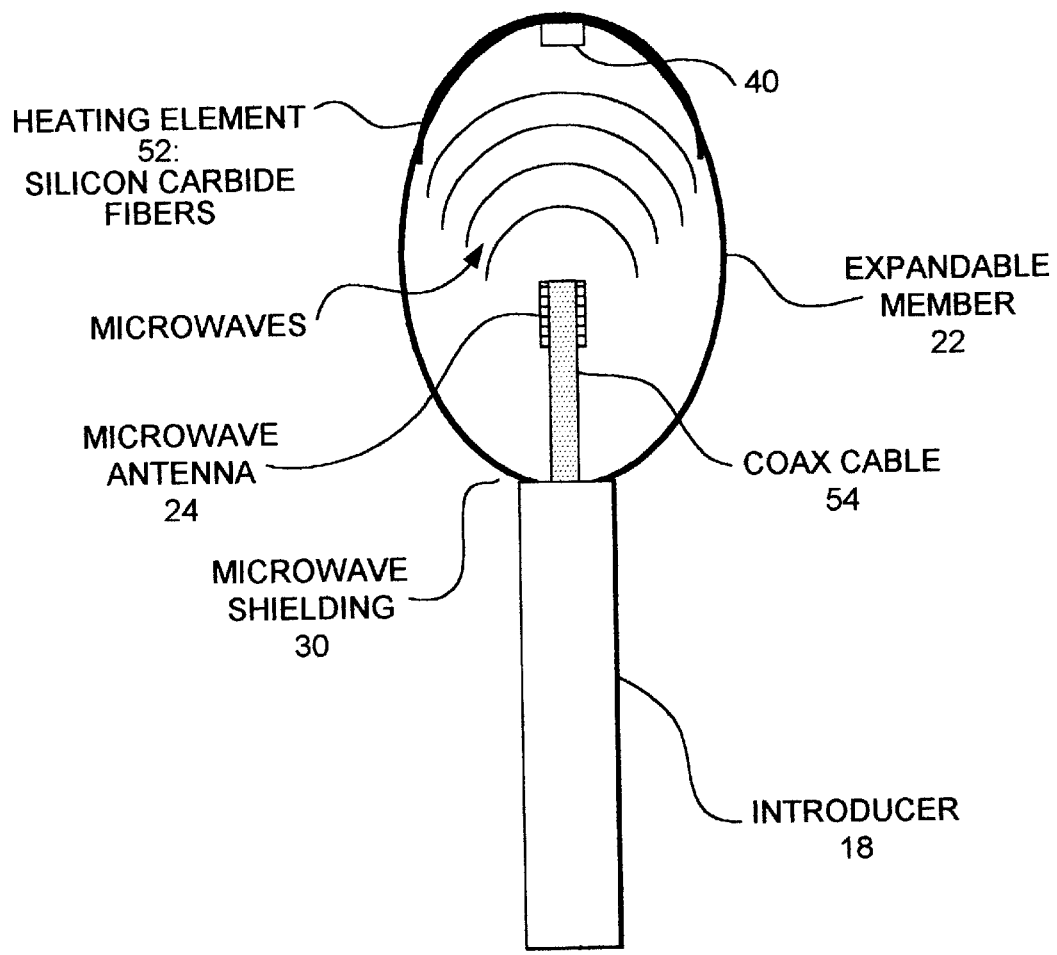
FIG. 10 is a lateral view illustrating the use of heating elements in the expandable member.

Referring now to FIG. 10 in another embodiment of the present invention, heating of uterine wall 23' may be done by heating elements 52, also called heating layer 52. Heating elements 52 are made of materials that are heated upon exposure to microwaves. The frequency and power of microwave energy form microwave power source 32 are adjustable to produce heating elements temperatures in the range of 45–90° C. The temperature of heating elements 52 can be controlled using control system 44 as will be discussed herein. This process can be facilitated by the use of sensors 40 be placed on or adjacent to heating elements 52. Suitable materials for heating elements 52 include graphite carbon, aluminum and ceramic fibers. Heating elements 52 can be located in all or a portion of the microwave chamber wall 20'''; or in all or a portion of the exterior or interior surface 20' and 20" of microwave chamber 20, which in this case may be integral to, or the same as conforming member 22. Heating elements 52 can be located inside microwave shielding layer 30. Alternatively heating elements 52 can be made of microwave absorbable materials such as silicon carbide and hence, make up microwave shielding layer 30. In an alternative embodiment, heating elements can be porous silicon carbide fibers which allow for the flow a liquid through heating elements for purpose of cooling heating elements 52. Similar to the distribution of pores 36, heating elements 52 can be located in discrete areas of expandable member 22 to in turn produce discrete thermal injury zones 14.

Figure 11:
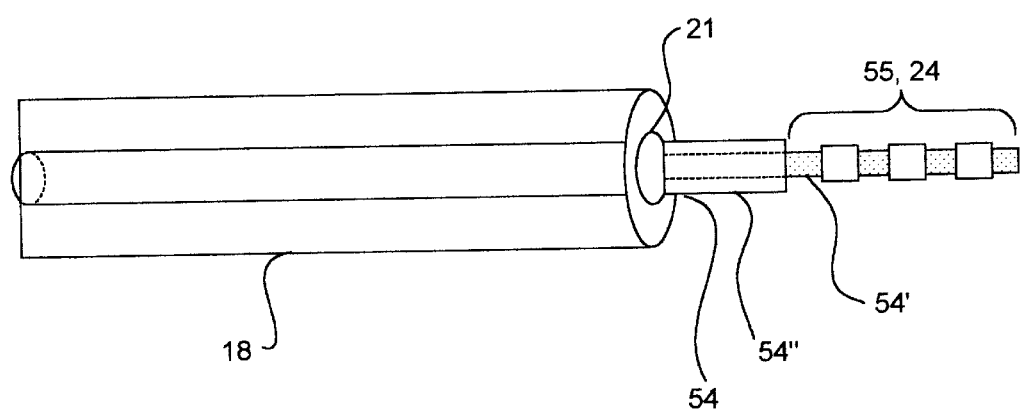
FIG. 11 is a lateral view illustrating the construction of the microwave antenna

Referring now to FIG. 11, microwave antenna 24 is typically a linear coaxial microwave antenna with a choke or a standard single junction dipole microwave antenna. The dipole microwave antenna 24 is constructed from a semi-rigid coaxial cable 54 having an inner conductor 54' covered by an insulator 54". Coaxial cable 54 from which the antenna 24, is formed extends from the proximal end of introducer 18 and terminates in the slotted radiating portion 55 of antenna 24. The operation of the dipole microwave antenna 24 as is utilized in the apparatus of the present invention is described more fully in U.S. Pat. No. 4,825,880 to Stauffer et. al. for an *Implantable Helical Coil Microwave Antenna,* which is incorporated herein by reference. In an alternative embodiment, microwave antenna 24 is movable within microwave chamber 20 by advancement of coaxial cable 54. In this embodiment antenna 24 can be increased or decreased in length by a sliding a sheath of microwave absorbable material (not shown) over antenna 24.

Microwave antenna 24 emits microwave energy at a preferred frequency of 1,300 MHz+−50 MHz, and at power levels adjustable up to 50 W or 100. Accordingly, the microwave power source 32 is capable of generating microwaves at a frequency of 1,300 MHz+−50 MHz. and can be set at a precise frequencies value within this range.

Figure 12:
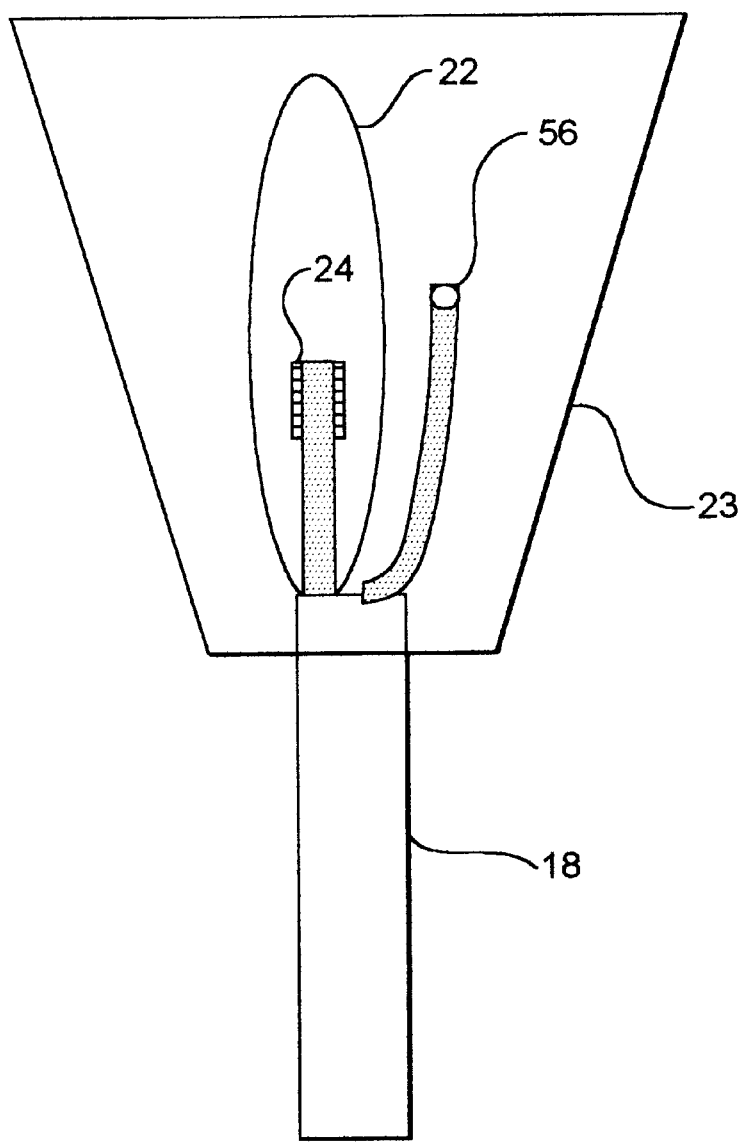
FIG. 12 is a cross sectional view illustrating a visualization device coupled to an embodiment of the invention.

Referring now to FIG. 12, another embodiment of uterine treatment apparatus 10 includes a visualization device 56 coupled to introducer 18. Visualization device 56 can include a combination of one or more of the following: a viewing scope, an expanded eyepiece, fiber optics (both imaging and illuminating fibers), video imaging devices and the like. Also, at least portions of uterine treatment apparatus 10 may be sufficiently radiopaque in order to be visible under fluoroscopy and/or sufficiently echogenic to be visible using ultrasonography.

Figure 13:
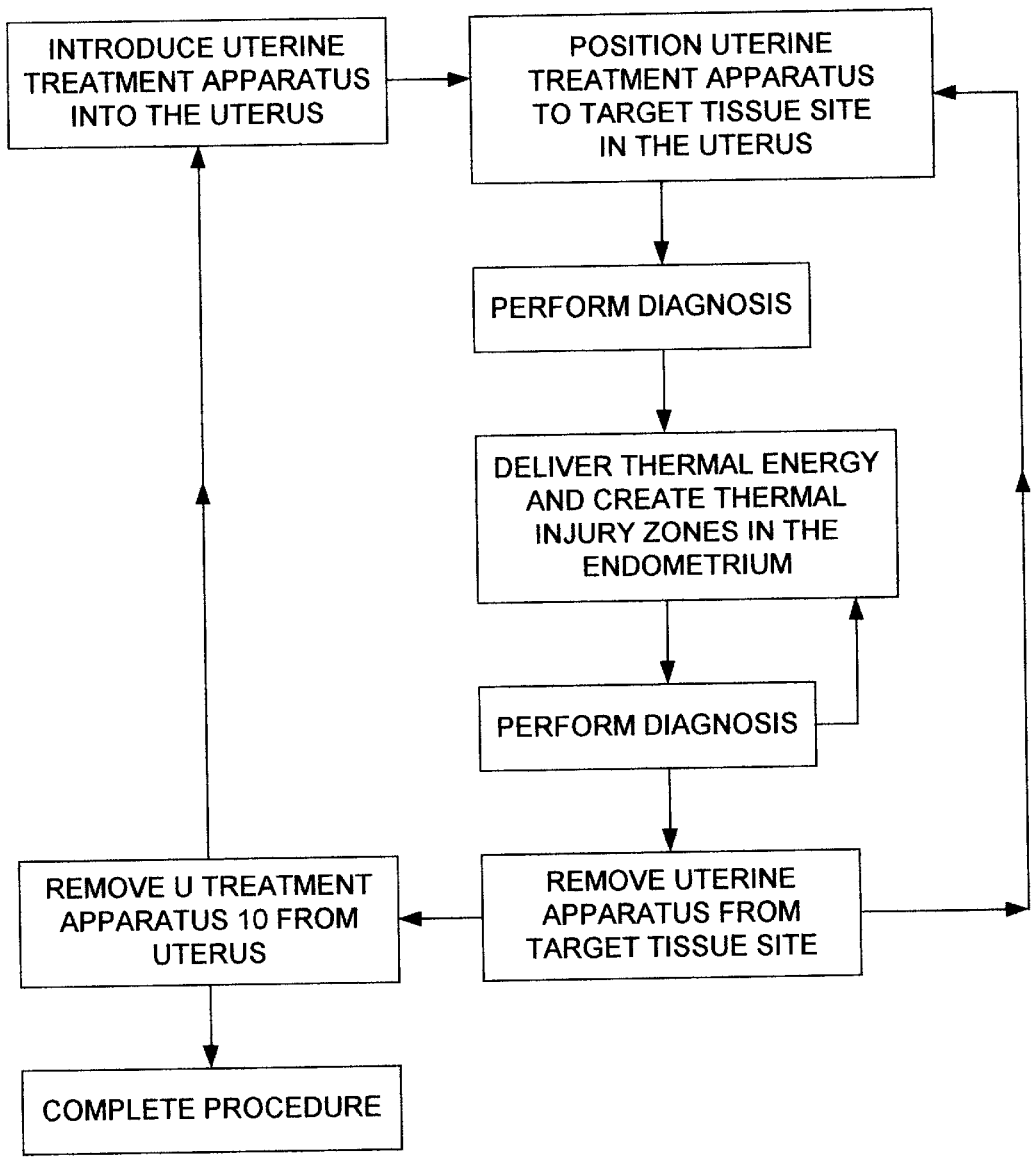
FIG. 13 is a flow chart illustrating a uterine treatment method using the apparatus of the present invention.

FIG. 13 is a flow chart illustrating one embodiment of the operation of uterine treatment apparatus 10. In this embodiment, treatment apparatus 10 is first introduced into the uterus under local anaesthesia which may be no more than a pericervical block or other local anesthetic known to those skilled in the art. With expandable member 22 in a non-deployed state, the distal portion of introducer 18 is advanced through the cervix 25 until expandable member 22 is positioned in the uterus 23. Sheath 29 is then withdrawn, and expandable member 22 is expanded with the introduction of a fluid such as heat transfer medium 34, causing expandable member 22 to become distended and be self-retained in the uterus 23.

Heat transfer medium 34 can be introduced into microwave chamber 20 at room temperature or preheated to a temperature which can be adjusted and modified as necessary, for example between 60 to 90° C. By heating heat transfer solution 34 prior to introduction into uterine treatment apparatus and or uterus 23, there is a reduction in the amount of time needed to complete a satisfactory thermal injury to uterine wall 23' and also to the total procedure time.

The diagnostic phase of the procedure then begins and can be performed using a variety of diagnostic methods known to those skilled in the art including the following: (i) visualization of the uterus 23 via an endoscope or other viewing apparatus inserted into the uterus 23, (ii) visualization of the interior morphology of the uterine wall 23' using ultrasonography to establish a baseline for the tissue to be treated, (iii) impedance measurement to determine the electrical conductivity between uterine wall 23' and uterine treatment apparatus 10.

After diagnosis, the treatment phase of the procedure begins. Heat transfer medium 34 is heated in microwave chamber 20 introduced into expandable member 22 through valve 42 or pores 36 and subsequently introduced into contact with uterine wall 23' through pores 36. Alternatively, heating elements 56 in or on expandable member 22 are heated and engaged with endometrium 16. Using either approach, the preferred uterine contact temperature to cause thermal injury is between 45 and 85° C. In this phase of the procedure, the delivery of thermal energy to treatment site 12 can be conducted under feedback control, manually or by a combination of both. Feedback can be included and is achieved by the use of one or more of the following methods: (i) visualization, (ii) impedance measurement, (iii) ultrasonography; (iv) temperature measurement; and, (v) contractile force measurement via manometry. The feedback mechanism permits the selected on-off switching of microwave power source 32 and/or fluid source 19.

The area and placement of thermal injury zones 14 in the uterine wall 23' can vary. However the degree of injury must be sufficient to necrose or irreparably damage all of the endometrial cells in the targeted tissue. It is further desirable that these are damaged sufficiently to be sloughed off or otherwise destroyed, and/or removed by wound healing cells of the body including: macrophage, fibroblasts and myofibroblasts. Regarding placement, thermal injury zone 14 may cover the entire endometrium or, alternatively, selected portions of the endometrium may not be ablated such as those portions close to the cervix and or the fallopian tubes. For both complete and partial ablation of endometrium 16, it is important that the thermal injury zones 14 are uniform with the respect to the degree of thermal injury of the tissue within the boundaries of the zone. It is particularly important that there are no areas of relatively uninjured endometrial tissue within the boundaries of thermal injury zone 14.

A second diagnostic phase may be included after the treatment is completed. This provides an indication of the uniformity of the thermal injury to the uterus, and whether or not a second phase of treatment, to all or only a portion of the uterus, now or at some later time, should be conducted. The second diagnostic phase is accomplished through one or more of the following methods: (i) visualization, (ii) measuring impedance. Once treatment is completed, expandable members 22 and 22" are evacuated of fluid and returned to their predeployed state and uterine treatment apparatus 10 is withdrawn from uterus 23.

This results in the uterus 23 returning to approximately its original shape.

Figure 14:
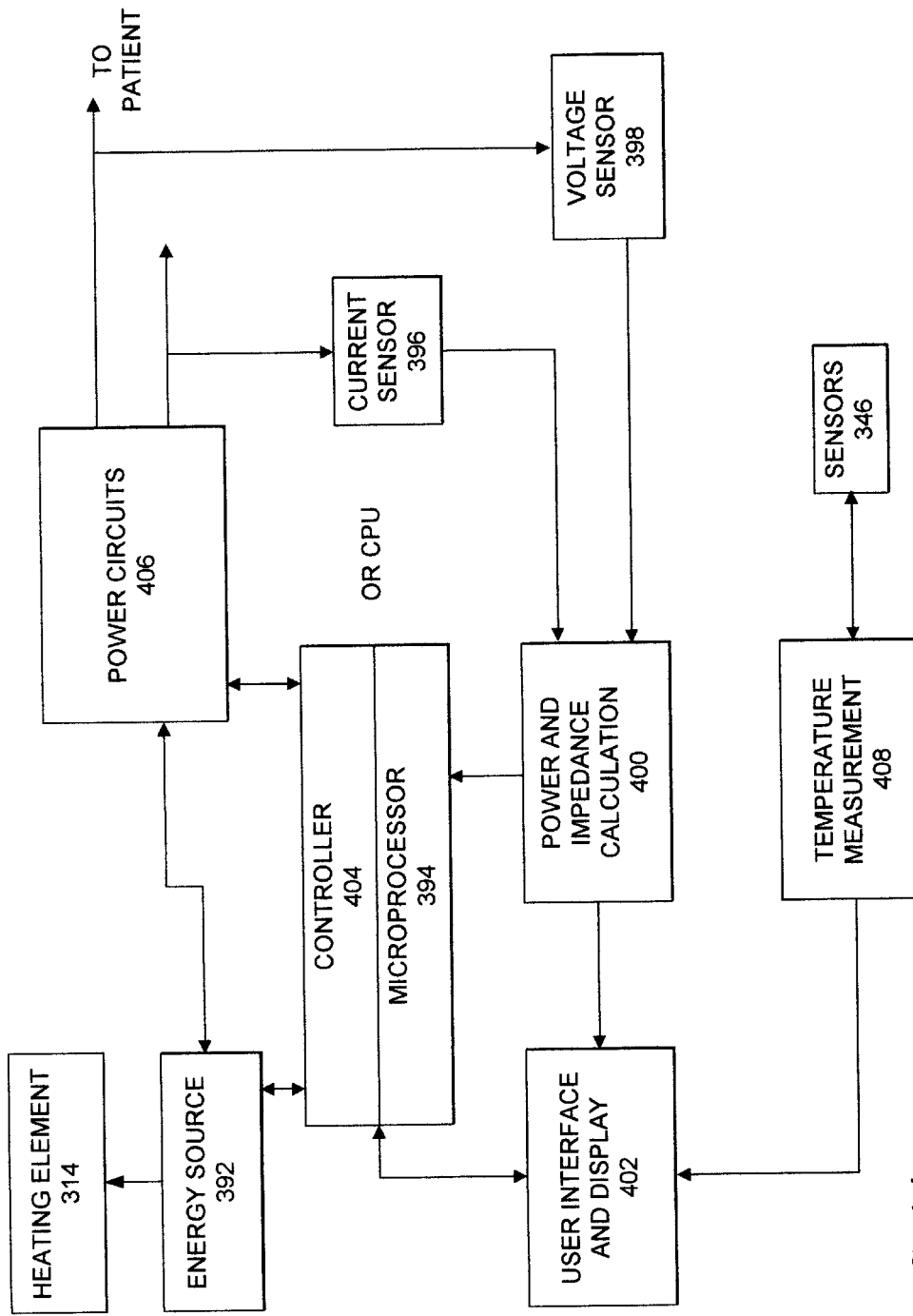
FIG. 14 depicts a block diagram of the feedback control system that can be used with the uterine treatment apparatus of the present invention.

Referring now to FIG. 14, an open or closed loop feedback system 44 couples sensor 40, now described as sensor 346, to an energy source 392. In this embodiment, an energy delivery device 314 is one or more heating elements 314; however, in various other embodiments, energy delivery device 314 may include others described herein. Similarly, in this embodiment, sensor 346 senses temperature, but in various other embodiments, sensor 346 may sense other physical properties described herein. In this embodiment, energy source 392 is a microwave energy source.

The temperature of the tissue, or of heating elements 314, is monitored, and the output power of energy source 392 adjusted accordingly. The physician can, if desired, override the closed or open loop system 44. A microprocessor 394 can be included and incorporated in the closed or open loop system to switch power on and off, as well as modulate the power. The closed loop system 44 utilizes microprocessor 394 to serve as a controller, monitor the temperature, adjust the microwave power, analyze the result, refeed the result, and then modulate the power.

With the use of sensor 346 and feedback control system 44, tissue adjacent to heating elements 314 can be maintained at a desired temperature for a selected period of time without causing a shut down of the power circuit to microwave energy source 392. Each heating element 314 is connected to resources which generate an independent output. The output maintains a selected temperature at heating elements 314 for a selected length of time.

Current delivered through heating elements 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404.

A control signal is generated by controller 404 that is proportional to the difference between an actual measured value, and a desired value. The control signal is used by power circuits 406 to adjust the power output an appropriate amount in order to maintain the desired power delivered at respective microwave energy source 392.

In a similar manner, temperatures detected at sensor 346 provide feedback for maintaining a selected power. Temperature at sensor 346 is used as a safety means to interrupt the delivery of power when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output an appropriate amount in order to maintain the desired temperature delivered at the sensor 346.

Controller 404 can be a digital or analog controller, or a computer with software. When controller 404 is a computer it can include a CPU coupled through a system bus. This system can include a keyboard, a disk drive, or other non-volatile memory systems, a display, and other peripherals, as are known in the art. Also coupled to the bus is a program memory and a data memory.

User interface and display 402 includes operator controls and a display. Controller 404 can be coupled to imaging systems including, but not limited to, ultrasound, CT scanners, X-ray, MRI, mammographic X-ray and the like. Further, direct visualization and tactile imaging can be utilized.

The output of current sensor 396 and voltage sensor 398 are used by controller 404 to maintain a selected power level at microwave energy source 392. The amount of energy delivered controls the amount of power. A profile of the power delivered to heating element 314 can be incorporated in controller 404 and a preset amount of energy to be delivered may also be profiled.

Circuitry, software and feedback to controller 404 result in process control, the maintenance of the selected power setting which is independent of changes in voltage or current, and is used to change the following process variables: (i) the selected power setting, (ii) the duty cycle (e.g., on-off time), (iii) bipolar or monopolar energy delivery; and, (iv) fluid delivery, including flow rate and pressure. These process variables are controlled and varied, while maintaining the desired delivery of power independent of changes in voltage or current, based on temperatures monitored at sensor 346.

Figure 15:
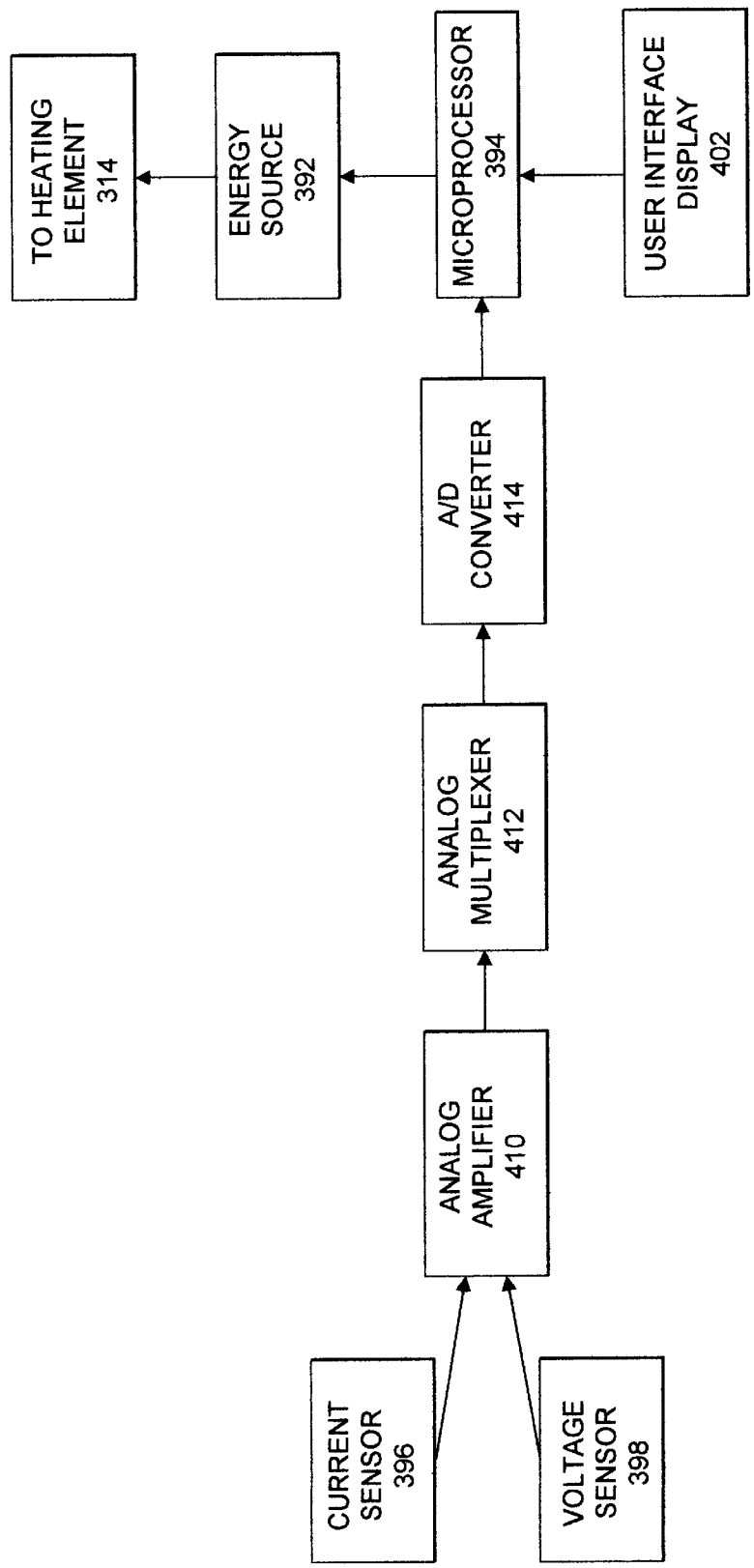
FIG. 15 depicts a block diagram of an analog amplifier, microprocessor and other electronic components used with the feedback control system of FIG. 14.

Referring now to FIG. 15, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage which represents the respective sensed temperatures. Digitized amplifier output voltages are supplied by A/D converter 414 to microprocessor 394. Microprocessor 394 may be a type 68HCII available from Motorola. However, it will be appreciated that any suitable microprocessor or general purpose digital or analog computer can be used to calculate impedance or temperature.

Microprocessor 394 sequentially receives and stores digital representations of impedance and temperature. Each digital value received by microprocessor 394 corresponds to different temperatures and impedances.

Calculated power and impedance values can be indicated on user interface and display 402. Alternatively, or in addition to the numerical indication of power or impedance, calculated impedance and power values can be compared by microprocessor 394 to power and impedance limits. When the values exceed predetermined power or impedance values, a warning can be given on user interface and display 402, and additionally, the delivery of microwave energy can be reduced, modified or interrupted. A control signal from microprocessor 394 can modify the power level supplied by energy source 392.

Figure 16:
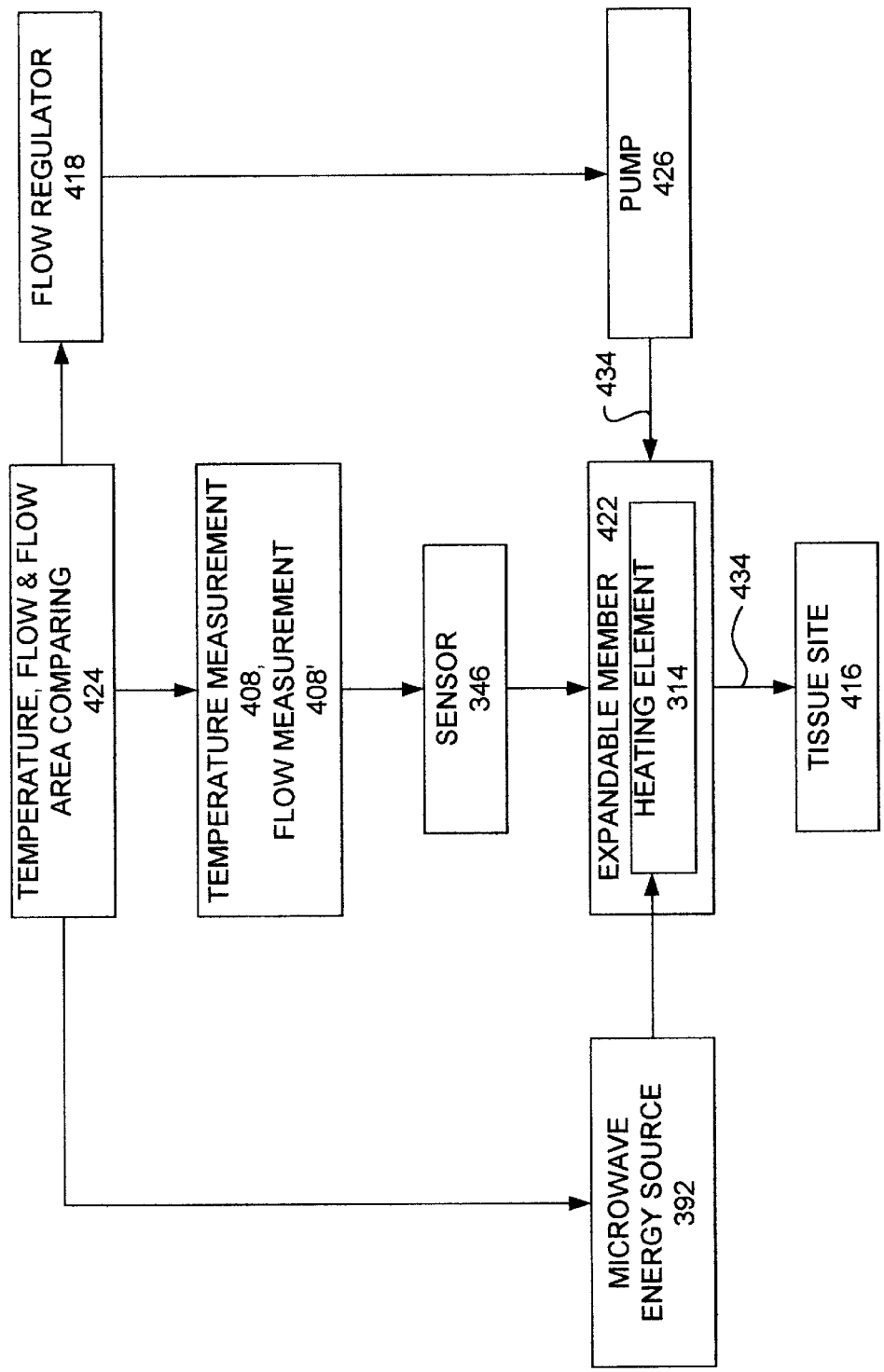
FIG. 16 depicts a block diagram of the operations performed in the feedback control system depicted in FIG. 14 including control of heat transfer medium flow and the flow area on the expandable member.

Referring now to FIG. 16, the control of the delivery of heat transfer medium 434 to tissue site 416 and the area of expandable member 422 that permeates heat transfer medium 434 is done in the following manner. During the application of energy and heat transfer medium 434, sensors 346 provides input to temperature measurement device 408 (which measures temperature) and flow measurement devices 408' (which measures the flow rate of heat transfer medium to tissue site 416 as well the total flowing area of expandable member 422). A comparator 424 receives a signal representative of the measured temperature, flow rate and flow area and compares these values to pre-set signals representative of the desired temperature, flow rate and flow area. If the measured, flow rate or flow area have not exceeded their desired levels, comparator 424 sends a signal to flow regulator 418 to maintain the flow rate and pressure head from electronically-controlled pump 426 at their existing levels. However, if the flow rate or flow area is too low, comparator 424 sends a signal to a flow regulator 418 connected to pump 426 representing a need for an increased flow rate and pressure head. Likewise, if the flow rate or flow area is too high, comparator 424 sends a signal to a flow regulator 418 connected to pump 426 representing a need for a decreased flow rate and pressure head.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A apparatus to treat a uterus, comprising:
    a first deployable member configured to be advancable and removable from a uterine cavity opening in a non-deployed state, the first deployable member further configured to be positioned in a uterine cavity in at least a partially deployed state to define a microwave chamber in an interior of the first deployable member, the first deployable member being at least partially microwave energy absorbable and formed of a fluid permeable material to house and controllably release a fluidic medium substantially positioned within the microwave chamber when the first deployable member is positioned in the uterine cavity in the at least partially deployed state;
    a microwave emitter positioned in the microwave chamber, the microwave emitter being configured to be coupled to a microwave energy source and deliver microwave energy to the fluidic medium, wherein the fluidic medium transfers thermal energy from the microwave emitter to a uterine structure.

2. The apparatus of claim 1, wherein the first deployable member provides a substantial confinement of microwave energy in the microwave chamber.

3. The apparatus of claim 1, wherein the fluid permeable material includes a microwave absorbable medium.

4. The apparatus of claim 1, wherein the first deployable member includes a fluid permeable member and a microwave absorbable member.

5. The apparatus of claim 4, wherein the microwave absorbable member is positioned in the microwave chamber.

6. The apparatus of claim 5, wherein the microwave absorbable member is positioned adjacent to the fluid permeable member.

7. The apparatus of claim 1, further comprising:
    a microwave reflectable member coupled to the first deployable member.

8. The apparatus of claim 7, wherein the microwave reflectable member has at least one of a shape, a material composition or a sufficient microwave reflectivity to enhance a heating rate of the fluidic medium in the microwave chamber.

9. The apparatus of claim 7, wherein the microwave reflectable member is positioned in the microwave chamber.

10. The apparatus of claim 7, wherein the microwave reflectable member is positioned at an exterior of the first deployable member.

11. The apparatus of claim 10, wherein the first deployable member includes a microwave absorbable member.

12. The apparatus of claim 1, wherein the first deployable member includes a fluid permeable member, a microwave reflectable member and a microwave absorbable member.

13. The apparatus of claim 1, wherein the first deployable member includes a fluid permeable member and a microwave reflective member.

14. The apparatus of claim 1, further comprising:
    a conformable member positioned at an exterior of the first deployable member.

15. The apparatus of claim 14, wherein the conformable member is at least partially made of a fluid permeable material.

16. The apparatus of claim 14, wherein the conformable member is made of a porous material.

17. The apparatus of claim 14, wherein the conformable member is made of a microporous material.

18. The apparatus of claim 1, further comprising:
    a deployable frame member positioned in the microwave chamber.

19. The apparatus of claim 1, wherein the fluidic medium is an electrolytic solution.

20. The apparatus of claim 19, wherein the electrolytic solution is a saline solution.

21. The apparatus of claim 1, further comprising:
    a sensor coupled to the first deployable member.

22. The apparatus of claim 21, wherein the sensor is a thermal sensor.

23. The apparatus of claim 21, further comprising:
a microwave energy source coupled to the microwave emitter; and
a feedback control configured to be coupled to the sensor and the microwave energy source.

24. The apparatus of claim 1, wherein the first deployable member is a balloon.

25. The apparatus of claim 1, further comprising:
an elongated member coupled to the first deployable member.

26. The apparatus of claim 25, wherein the elongated member includes a fluidic medium infusion lumen.

27. The apparatus of claim 1, further comprising:
a second deployable member positioned at an exterior of the first deployable member.

28. The apparatus of claim 27, wherein the second deployable member is configured to be at least partially confirming to the uterine cavity in the deployed state.

29. The apparatus of claim 27, wherein the second deployable member is made of a fluid permeable material.

30. The apparatus of claim 27, wherein the second deployable member is at least partially conforming to the uterine cavity in the deployed state.

31. The apparatus of claim 27, wherein the second deployable member is made of a fluid permeable material.

32. The apparatus of claim 1, further comprising:
a valve member coupled to the first deployable member.

33. The apparatus of claim 32, wherein the valve member provides a control flow of fluidic medium out of the microwave chamber into the second deployable member.

34. The apparatus of claim 33, wherein the valve member provides a control flow of fluidic medium into and out of the microwave chamber.

35. The apparatus of claim 1, wherein the first deployable member is sufficiently microwave energy reflective to provide an enhanced microwave chamber.

36. A apparatus to treat a uterus, comprising:
an introducer including an introducer lumen;
a first deployable member configured to be positioned in the introducer lumen in a non-deployed state, the first deployable member configured to be positioned in a uterine cavity and expand to a deployed state upon an introduction of a fluidic media into a microwave cavity defined by an interior of the first deployable member, the first deployable member being at least partially microwave energy absorbable and formed of a fluid permeable material to controllably release a fluidic media substantially positioned within the microwave chamber to a uterine structure; and
a microwave emitter positioned in an interior of the first deployable member, the microwave emitter being configured to be coupled to a microwave energy source and deliver microwave energy to the fluidic media, wherein the fluidic media transfers thermal energy from the microwave emitter to a uterine structure.

37. The apparatus of claim 36, wherein the introducer is flexible.

38. The apparatus of claim 36, wherein the first deployable member has at least one of a shape, or a material composition to provide a substantial confinement of microwave energy in the microwave chamber.

39. The apparatus of claim 36, wherein the fluid permeable material includes a microwave absorbable medium.

40. The apparatus of claim 36, wherein the first deployable member includes a fluid permeable member and a microwave absorbable member.

41. The apparatus of claim 40, wherein the microwave absorbable member is positioned in the microwave chamber.

42. The apparatus of claim 41, wherein the microwave absorbable member is positioned adjacent to the fluid permeable member.

43. The apparatus of claim 36, further comprising:
a microwave reflectable member coupled to the first deployable member.

44. The apparatus of claim 43, wherein the microwave reflectable member has at least one of a shape, a material composition or a sufficient microwave reflectivity to enhance a fluidic medium heating rate in the microwave chamber.

45. The apparatus of claim 43, wherein the microwave reflectable member is positioned in the microwave chamber.

46. The apparatus of claim 43, wherein the microwave reflectable member is positioned at an exterior of the first deployable member.

47. The apparatus of claim 46, wherein the first deployable member includes a micro wave absorbable member.

48. The apparatus of claim 36, wherein the first deployable member includes a fluid permeable member, a microwave reflectable member and a microwave absorbable member.

49. The apparatus of claim 36, wherein the first deployable member includes a fluid permeable member and a microwave reflective member.

50. The apparatus of claim 36, further comprising:
a conformable member positioned at an exterior of the first deployable member.

51. The apparatus of claim 50, wherein the conformable member is at least partially made of a fluid permeable material.

52. The apparatus of claim 50, wherein the conformable member is made of a porous material.

53. The apparatus of claim 50, wherein the conformable member is made of a microporous material.

54. The apparatus of claim 36, further comprising:
a deployable frame member positioned in the microwave chamber.

55. The apparatus of claim 36, wherein the fluidic medium is an electrolytic solution.

56. The apparatus of claim 55, wherein the electrolytic solution is a saline solution.

57. The apparatus of claim 36, further comprising:
a sensor coupled to the first deployable member.

58. The apparatus of claim 57, wherein the sensor is a thermal sensor.

59. The apparatus of claim 57, further comprising:
a microwave energy source coupled to the microwave emitter and a feedback control configured to be coupled to the sensor and the microwave energy source.

60. The apparatus of claim 36, wherein the first deployable member is a balloon.

61. The apparatus of claim 36, further comprising:
an elongated member coupled to the first deployable member.

62. The apparatus of claim 61, wherein the elongated member includes a fluidic medium infusion lumen.

63. The apparatus of claim 36, further comprising:
a second deployable member positioned at an exterior of the first deployable member.

64. The apparatus of claim 36, further comprising:
a valve member coupled to the first deployable member.

65. The apparatus of claim 64, wherein the valve member provides a control flow of fluidic medium out of the microwave chamber into the second deployable member.

66. The apparatus of claim 36, wherein the first deployable member is sufficiently microwave energy reflective to provide an enhanced microwave chamber.

* * * * *